US00PP28625P3

(12) United States Plant Patent
Khayat

(10) Patent No.: US PP28,625 P3
(45) Date of Patent: Nov. 14, 2017

(54) BANANA PLANT NAMED 'RA'

(50) Latin Name: *Musa acuminata*
Varietal Denomination: RA

(71) Applicant: Eliyahu Khayat, Nahariya (IL)

(72) Inventor: Eliyahu Khayat, Nahariya (IL)

(73) Assignee: Rahan Meristem (1998) LTD, Rosh Hanikra (IL)

( * ) Notice: Subject to any disclaimer, the term of this patent is extended or adjusted under 35 U.S.C. 154(b) by 386 days.

(21) Appl. No.: 14/544,407

(22) Filed: Jan. 3, 2015

(65) Prior Publication Data

US 2016/0198605 P1 Jul. 7, 2016

(51) Int. Cl.
*A01H 5/08* (2006.01)

(52) U.S. Cl.
USPC ..... Plt./160

(58) Field of Classification Search
USPC ..... Plt./160
CPC ..... A01H 5/08
See application file for complete search history.

(56) References Cited

U.S. PATENT DOCUMENTS

PP20,645 P3 1/2010 Khayat
8,097,773 B2 1/2012 Khayat

OTHER PUBLICATIONS

Meredith, Lawrence, Trans. Br. mycol. Soc. 52 (3),459-476 (1969) Printed in Great Britain, Black Leaf Streak Disease of Bananas (*Mycosphaerella fijiensis*): Symptoms of Disease in Hawaii, and Notes on the Conidial State of the Causal Fungus.

Khayat et al, Somoclonal variation in banana . . . genetic mechanism, frequency, . . . a tool for clonal selection, Agriculture and Consumer Protection; FAO Corporate Document Repository; 2004; 12 pages.

Churchill; Mycosphaerella fijiensis, the black leaf streak pathogen of banana: progress towards understanding pathogen biology and detection, disease developement, and the challanges of control; Molecular Plant Pathology; 2010; pp. 1-22.

*Primary Examiner* — Kent L Bell
(74) *Attorney, Agent, or Firm* — Lyn Marantz; KK Patents, LLC

(57) ABSTRACT

'RA' is a cultivar of the ancestral banana line 'Gran Nain' (GN), which belongs to *Musa acuminata* variety 'Cavendish'. When compared to its ancestral line, 'RA' shows the following characteristics:

1. Super heavy fruit bunch,
2. Especially long, and heavy fingers in a hand,
6. More fingers per hand,
3. Wavy leaf lamina,
7. Youngest unfolded leaves are tightly rolled,
8. Thicker pseudostem circumference,
9. Higher fruit yield per bunch,
10. More cylindrical bunch shape.

19 Drawing Sheets

*Musa acuminata* (AAA) cultivated variety Cavendish 'RA'.

BACKGROUND OF THE INVENTION

Field of the Invention

'RA' is a triploid banana plant belonging to *Musa acuminata* (AAA) variety Cavendish. The 'RA' clone is a mutant of the earlier selection Gran Nain originating in the Western Galilee, Israel. This mutant was created by an extensive process of tissue culture. The retro-transposing element expression was used as a marker in the selection process (ii). The 'RA' line was primarily selected on the basis of its fruit size, bunch weight, architecture and the quality of the fruit.

'RA' was created using the tissue culture technology as specified below.

i. A single distinctive plant was found in a banana plantation of the cultivated variety Gran Nain in the western Galilee, Israel. This plant's distinctive merits were its super large bunch and long fingers.

ii. A meristem from this plant was harvested when the shoot reached 45 cm from the ground. This meristem was disinfected by immersion in 0.3% commercial sodium hypochlorite solution for 30 minutes, followed by several rinses with sterile distilled water. The disinfection process was repeated three times as per above and subsequently the meristem (0.5×0.5 cm) was placed on a solid medium containing MS salts, 0.3% w/v sucrose, 10 $mg \cdot L^{-1}$ benzyladenine, 1 mg $L^{-1}$ thidiazuron (TDZ), and MS vitamins (multiplication medium).

iii. The meristem was incubated for 4 weeks at 22° Celsius under florescent lighting in a regime of 16/8 dark/light hours. The meristem was subdivided longitudinally into 3 sub-meristems that were each cultured separately. Each of the 3 sub-meristems was incubated for an additional 4 weeks in conditions as described above.

iv. Following 24 subcultures as indicated in step iii, the subcultured meristems were transferred onto a medium that contained MS salts, 0.1 $mg \cdot L^{-1}$ kinetin, MS vitamins, and 0.1 $mg \cdot L^{-1}$ 1-naphthaleneacetic acid (NAA) (rooting and regeneration medium). The 24 subcultures in the presence of 10 mg·L$^{-1}$ BA and 1 mg·L$^{-1}$ TDZ induce somaclonal variations (Khayat, 2004).

v. After 4 weeks of culture in the rooting and regeneration medium, under the environmental conditions indicated in step iii, the plants were individually placed in 10 cm$^3$ peat moss plugs in a greenhouse under mist irrigation. After an additional 4 weeks of growth, each plant was placed in a 5 L pot and let grow until it reached the height of about 60 cm.

vi. At 60 cm. in height, the plants were removed from the pots and planted in the field in Kibbutz Rosh Hanikra Western Galilee, Israel, at a density of approximately 200 plants per 1000 m$^2$. The total population consisted of 1500 plants.

vii. The resulting population was planted in the field (Western Galilee) and selected for:

1. High bunch weight
2. Open fingers in each hand on a bunch
3. Long and thick fingers
4. Early flowering and fruit maturation viii. Four plants were selected from the entire population (1500 plants). The meristems from these plants were placed in culture and propagated to 500 plants per single meristem.

ix. The new population of 500 plants was reselected from the field and the best performing plant according to the above criteria (see vii) was placed in culture and propagated to 500 plants that were examined for clonal stability. This population is distinctly different from 'Gran Nain' maintaining a significantly higher bunch weight and longer fingers. In addition, the population exhibited low deviation from the mean with respect to bunch weight and finger length.

The 'RA' selection was performed in Rosh Hanikra, the Western Galilee, Israel; by mutating an earlier selection known as 'Gran Nain', in 2007-2008. The mutation resulted as a consequence of multiple subcultures in vitro. This type of mutation known as somaclonal variation is induced by an extensive process of tissue culture (ii).

Banana and plantains (*Musa* spp.) comprise major food sources for more than 400 million people worldwide. Of the huge volume of fruit production approximately 15% is exported to remote markets. Most banana and plantains are inter or intra hybrids between two species namely *Musa acuminata* (A genome) and *Musa balbisiana* (B genome). By far, the most important export variety is Cavendish (a triploid AAA). In the 1950's, this variety replaced 'Gros Michel' which was almost wiped out due to attacks from a new strain of the fungal disease, *Fusarium* Wilt. Being resistant to the disease combined with wide consumer acceptance in export markets made 'Cavendish' irreplaceable. Due to double sterility and the triploid nature of 'Cavendish', breeders have very limited tools to improve the germplasm of this variety. Consequently, 'Cavendish' bananas suffer from a variety of pests and diseases. Due to the inability of 'Cavendish' to cross hybridize there are very limited sources of variability. In addition, in the cultivated variety 'Gran Nain', the fruit bunch is conical, i.e. the lower hands are smaller than the middle hands above them. As a result, the only hands that are saleable in the export market are the upper hands, while the lower 2 to 3 hands do not reach the standard size for the export market. Consequently, banana growers benefit only from approximately 60%-80% of the fruit on a bunch. The rest is discarded due to the fruit being too short and thin to have requisite export market value. Beyond the loss of yield due to every bunch having undersized fruit, there is also a labor cost to remove this undesirable fruit. "Finger" size is a very important qualitative parameter. For instance, most European countries require a standard minimum 17.5 cm for acceptance in the markets. The accepted rule in the 'Cavendish' banana fruit export market is a value on larger fruit. Larger fruit is a measure of higher quality and obtains a premium market price. In addition, during shipment, due to the fruit abrading against each other, in each hand as well as between the hands, the fruit become damaged and looses quality, therefore becoming unmarketable in the export marketplace. Consequently, banana growers and merchants prefer hands having well spaced fingers, and bunches having separated hands. An additional parameter appreciated by banana merchants is maximal weight of each fruit finger in a hand. Market pressure requires that the fingers be uniform, heavy, long, and not abraded.

Based on somaclonal variation, breeders have selected clones that exhibit better traits in the offspring in comparison to the wild type. Given that these chromosomal changes do not involve recombination events, they are rare and restricted to a narrow range of phenotypic variations. Even with extensive tissue culture cycling, the rate of variation is low and entirely unpredictable. Nevertheless, some selected clones are highly desired by banana growers due to their high performance, mainly in terms of yield and plant architecture. Among the most popular selections 'Gal', 'Jaffa', (U.S. Pat. No. 8,097,773 B2) and 'Adi' (U.S. Plant Pat. No. 20,645 P3) are widely used throughout the world. These last three selections were achieved using a unique genetic tool that has been developed to validate high enough levels of mutations in the "in vitro" processed material (ii). This discovery was achieved through elucidation of a mode of mutation that involves expression of a retro-transposing element known as BanR1 element.

The somaclone 'RA', developed by the inventors, is a unique 'Cavendish' selection due to its extremely long fingers, open separation of fingers in a hand, well separated hands in a bunch, and uniform size along a cylindrical shaped bunch.

The agri-technical properties of the 'Gran Nain' line as well as its genetic instability make it a good candidate as an originator of the new selection. 'Gran Nain' is also known for its intermediate stature, its fast return from appearance of sucker to development of the fruit and for its high response to optimal water and fertilizer regimens. In TABLE 1 below, there is a comparison of various plant architecture parameters between the common cultivars 'Gran Nain', 'Jaffa', 'Gal', 'Adi', and 'RA', all grown in the same location under the same cultivation procedure at the same time.

TABLE 1

| Cultivar | Number of plants | Average Height cm | Average Bunch Weight kg | Average Finger Length cm | Average Finger Weight gm | Date of Flowering | Weeks to Harvest |
|---|---|---|---|---|---|---|---|
| RA | 167 | 330 | 58.5 | 27.4 | 229.0 | Aug. 5 | 10 |
| ADI | 148 | 240 | 47.8 | 23.5 | 189.6 | Aug. 5 | 10 |
| GAL | 102 | 320 | 43.0 | 24.5 | 183.5 | Jul. 29 | 11 |
| JAFFA | 155 | 390 | 50.6 | 25.9 | 196.4 | Jul. 29 | 11 |
| GRAN NAIN | 400 | 320 | 42.5 | 20.2 | 179.8 | Jul. 29 | 9 |

Description of Relevant Prior Art

The data shows that 'RA' is similar to 'Gran Nain' in most parameters except for the finger size and fruit bunch architecture. The unique characteristics of the 'RA' are improvements in fruit quality and increased total marketable yield. These characteristics are demonstrated by a larger finger size for the entire bunch including the lower hands. This is a dramatic improvement as the lower hands are traditionally wasted in 'Gran Nain'. Larger finger size in all the hands enables the grower to benefit from commercialization of the lower hands in the bunch FIG. 1.

'RA' is easily recognizable in the field due to the wavy morphology of the leaf lamina FIG. 2. This morphology contributes to a larger leaf size index for the same leaf area. In a dense banana plantation the wavy structure of the leaf contributes to a higher light interception index on the leaf surface in a given leaf area. Another important characteristic of 'RA' is its higher number of fingers in a hand compared to its originator 'Gran Nain' FIG. 3. An additional feature of 'RA' is the morphology of the newly developed leaves in a mature plant. Unlike 'Gran Nain' the phenotype of the newest leaves in 'RA' FIG. 4 is very compactly rolled, resulting in a very small portion of the leaf lamina being exposed to the outside compared to 'Gran Nain' which is very loosely folded with approximately half of its leaf lamina exposed.

This new cultivar 'RA', was asexually produced from corms using the tissue culture procedure developed by the inventors in in Rosh Hanikra, Israel. 'RA' characteristics have been proven stable in the field for at least four consecutive generations.

SUMMARY OF THE INVENTION

In the present invention we describe a distinct elite Cavendish cultivar, 'RA', that combines a super heavy bunch, especially long, thick and heavy fingers, with more fingers per hand, wavy leaf lamina, with the youngest leaf tightly rolled, thicker pseudostem circumference, and a higher fruit yield per bunch.

BRIEF DESCRIPTION OF THE DRAWINGS

FIG. 4 also shows an 'RA' plant and a 'GN' plant side by side, 5 months post planting, prior to flower initiation.

The most apparent distinguishing morphological features between 'RA' and its originator GN are the yield, finger size and weight, and bunch structure as shown in FIG. 1, FIG. 3, FIG. 5, FIG. 6, FIG. 7, FIG. 8, FIG. 9, FIG. 10, FIG. 11, FIG. 12, and FIG. 13. These FIGS. express the components that contribute to 'RA''s higher yield compared to 'GN'. The major distinguishing component between 'RA' and 'GN' is finger size. The average finger weight of 'RA' is significantly higher than in 'GN' amounting to approximately 22% more weight in 'RA' fingers compared to the weight of 'GN' fingers FIG. 10. This phenomenon is due to longer fingers in the 'RA' (approximately 26% longer than 'GN') FIG. 6, while the fruits circumference does not differ significantly FIG. 8. The export market requires a minimum of 21 cm in length per finger to qualify as grade "A" fruit. Note, in FIG. 13 hand #12 is always marketable in 'RA' but typically not marketable in 'GN'. The higher finger weights combined with the higher number of marketable hands per bunch in 'RA' results in approximately 20% higher marketable yield for the 'RA' compared to 'GN' FIG. 6, FIG. 7. Despite the fact that the number of hands is similar, the 'RA' provides a better yield to the grower due to the longer fingers in all the hands, especially in the lowest hands.

Figure 1:
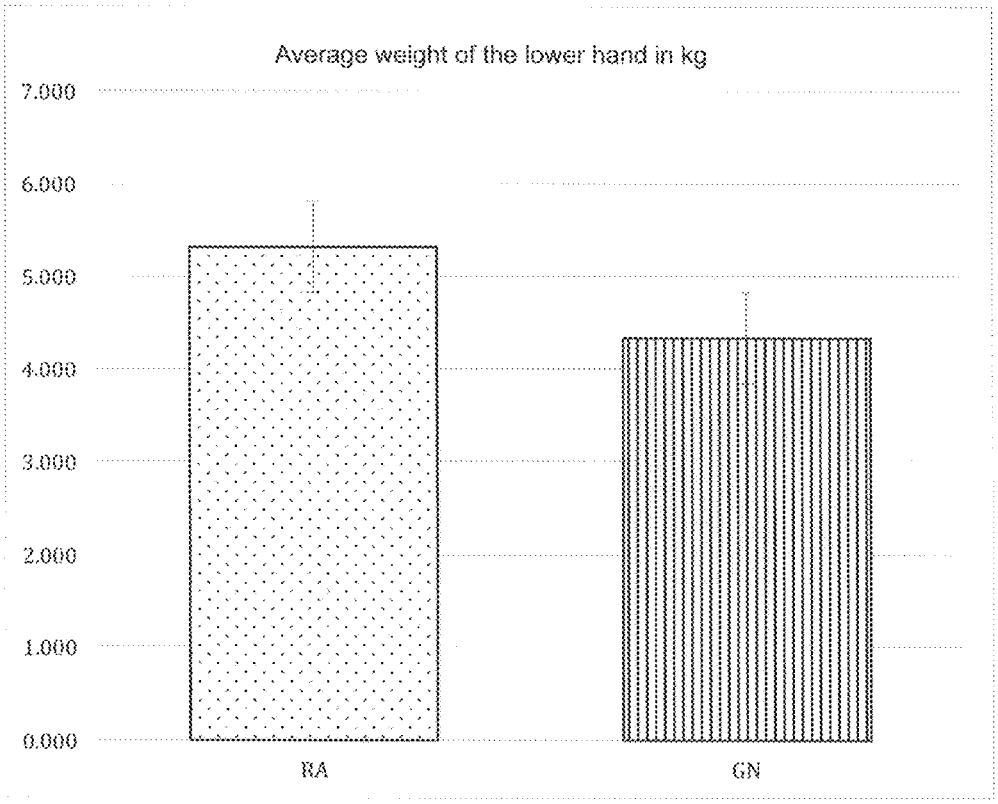
FIG. 1 shows the average weight (kg) of the lowest hand of 'RA' and 'Gran Nain' (GN) banana bunches.

FIG. 1: Average weight (kg) of the lowest hand (hand #12) on a bunch of banana (*Musa acuminata* AAA, cv. Cavendish) cultivars 'RA' and 'GN'. Banana plants were grown under a net in a commercial field in the Western Galilee, Israel. Measurements were performed at harvest of the second cycle of production (15 months after planting) in November 2013. Values represent the mean hand weight from 35 plants in each of the cultivars 'RA' and 'GN'±standard error. Fertigation and other cultural applications were carried out according to commercial banana plantation practices in the Western Galilee, Israel.

Figure 2:
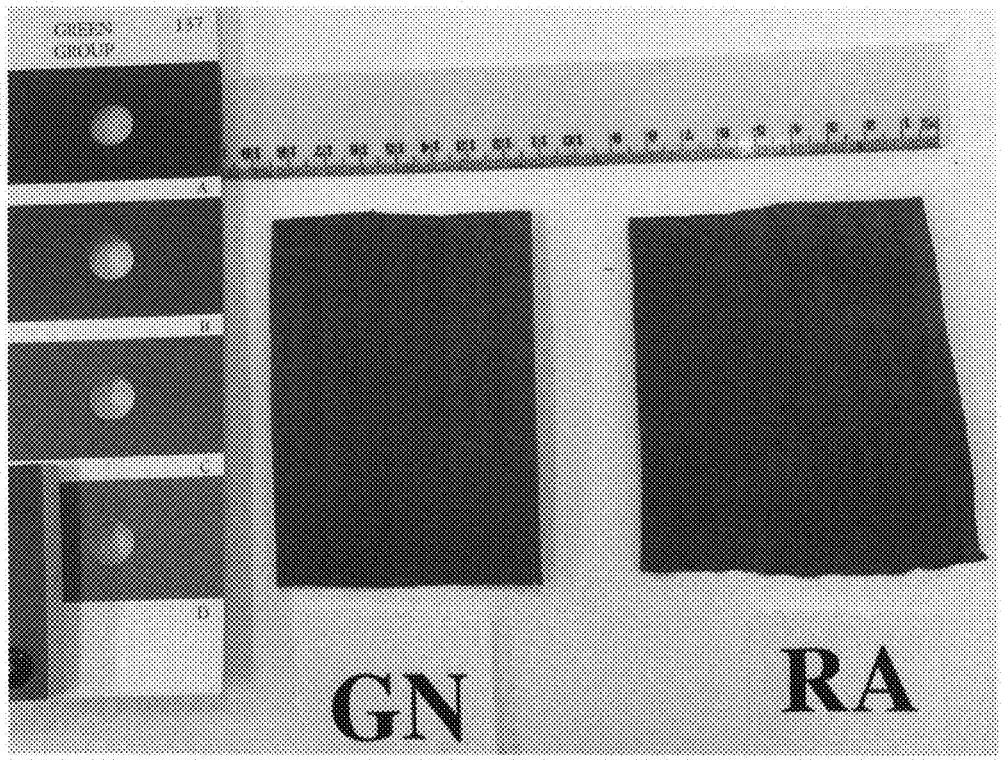
FIG. 2 shows the wavy morphology of 'RA' leaf lamina compared to the flat leaves of 'GN'.

The leaf lamina in 'GN' is flat while the 'RA' leaf shows a wavy surface phenotype as demonstrated in FIG. 2. The wavy leaf characteristic allows the leaf to have more light interception on the surface of the leaf per unit area of the leaf. Given the high density of planting in banana plantations (up to 2000 plants per hectare) light interception per leaf area is an important factor to photosynthesis and total fixation of carbon dioxide.

FIG. 2 shows the wavy morphology of 'RA' leaf lamina compared to the flat leaves of 'GN'. The comparison was performed on the second youngest fully expanded leaf in both cultivars. For both 'Gran Nain' and 'RA' the leaf lamina of the 3rd fully expended youngest leaf was cut in the middle portion of the leaf 10 cm from the main vein. Banana plants were grown under a net in a commercial field in the Western Galilee Israel. Photos were taken at harvest of the first cycle of production (15 months after planting) in November 2013. Fertigation and other cultural applications were carried out according to commercial banana plantation practices in the Western Galilee (Israel).

Figure 3:
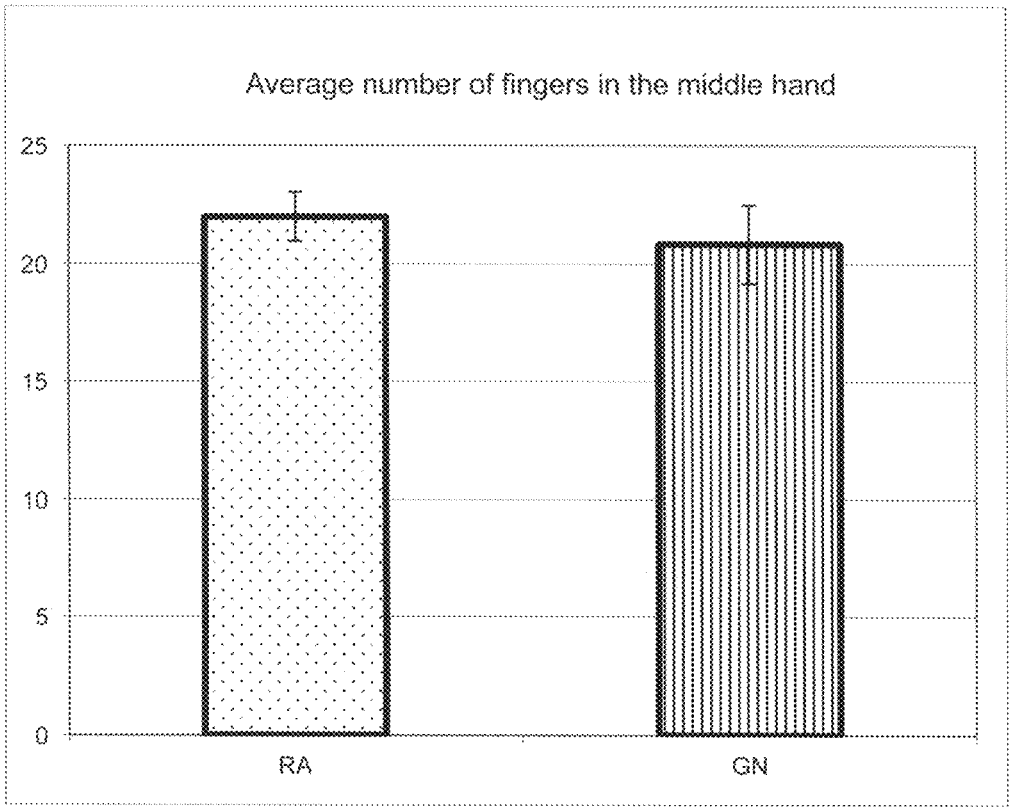
FIG. 3 shows the average number of fingers in the middle hand of 'RA' and 'GN' banana bunches.
Figure 11:
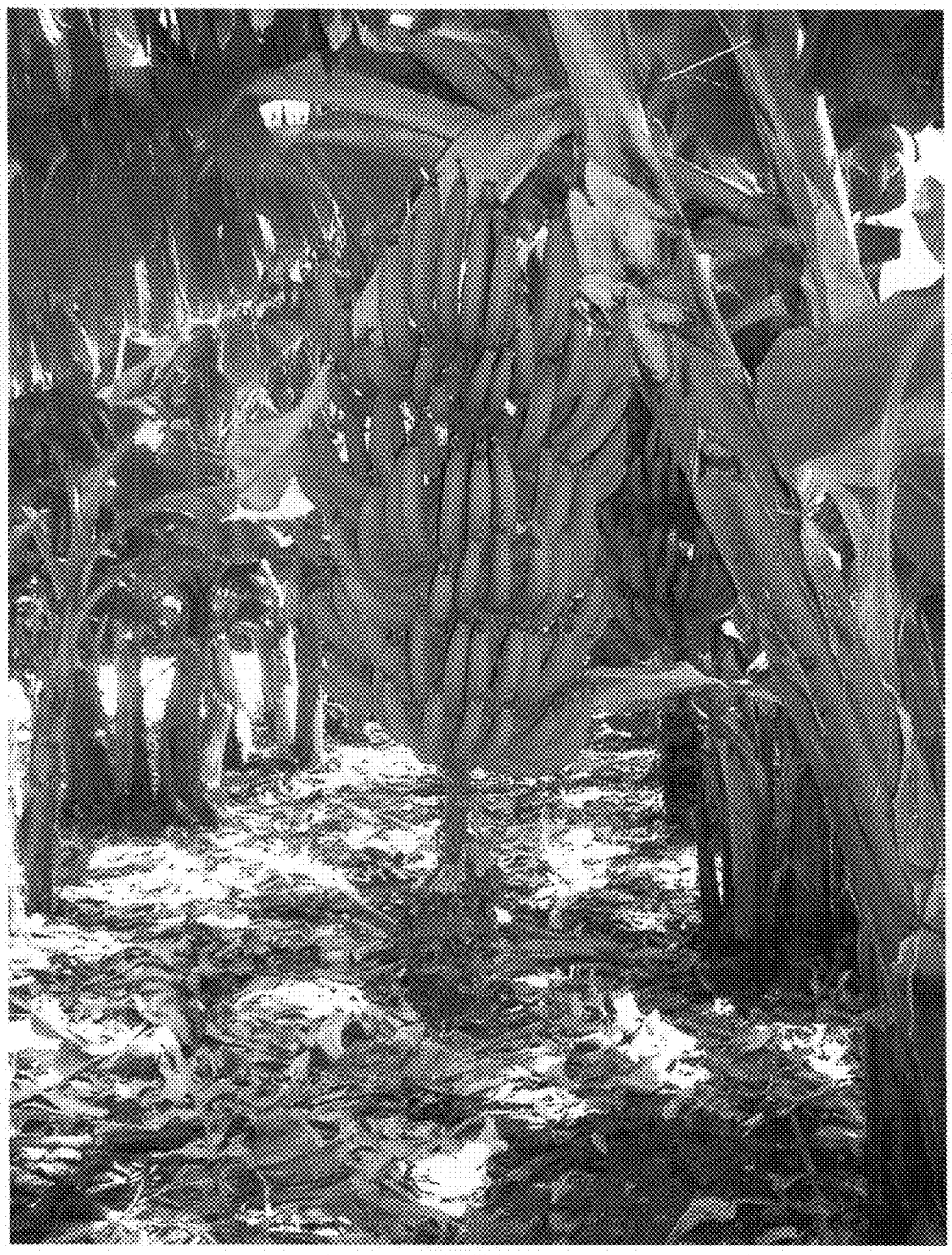
FIG. 11 shows a typical 'RA' banana plant including a fruit bunch, approximately 1 month prior to harvesting.

FIG. 3: Shows the average number of fingers in the middle hand of 'RA' and 'GN' banana (*Musa acuminata* AAA, cv. Cavendish) fruit at time of harvest. Banana plants were grown under a net in a commercial field in the Western Galilee Israel. Measurements were performed at harvest of the first cycle of production (15 months after planting) in November 2013. Values represent the average number of fingers from 35 plants in each of the selections 'RA' and 'GN'±standard error. Fertigation and other cultural applications were carried out according to commercial banana plantation practices in the Western Galilee (Israel). FIG. 3 shows that the average number of fingers in a hand is 10% higher in 'RA' in comparison to 'GN'. It is common practice to remove at least one of the lowest hands in the bunch prior to fruit fill in the field due to its short finger length. In the case of 'RA', this practice is unnecessary due to the cylindrical shape of the bunch FIG. 11 compared to the conical shape of the fruit bunch in 'GN' FIG. 12.

Another important feature of 'RA' is the tightly rolled youngest leaf. This structure results in minimal leaf surface exposure of the outside of the youngest leaf FIG. 4. Prior art shows that the site of infection by spores of *Mycosphaerella fijiensis*, the most severe 'Cavendish' disease, is the abaxial side of the youngest unfolded leaf (Churchill 2010). Meredith and Lawrence (1969) have described the stages of development of black leaf streak disease. In their publication, they indicated that the site of infection is the youngest unfolded leaf. This characteristic may contribute to retardation of progression of the Black Sigatoka disease.

Figure 4:
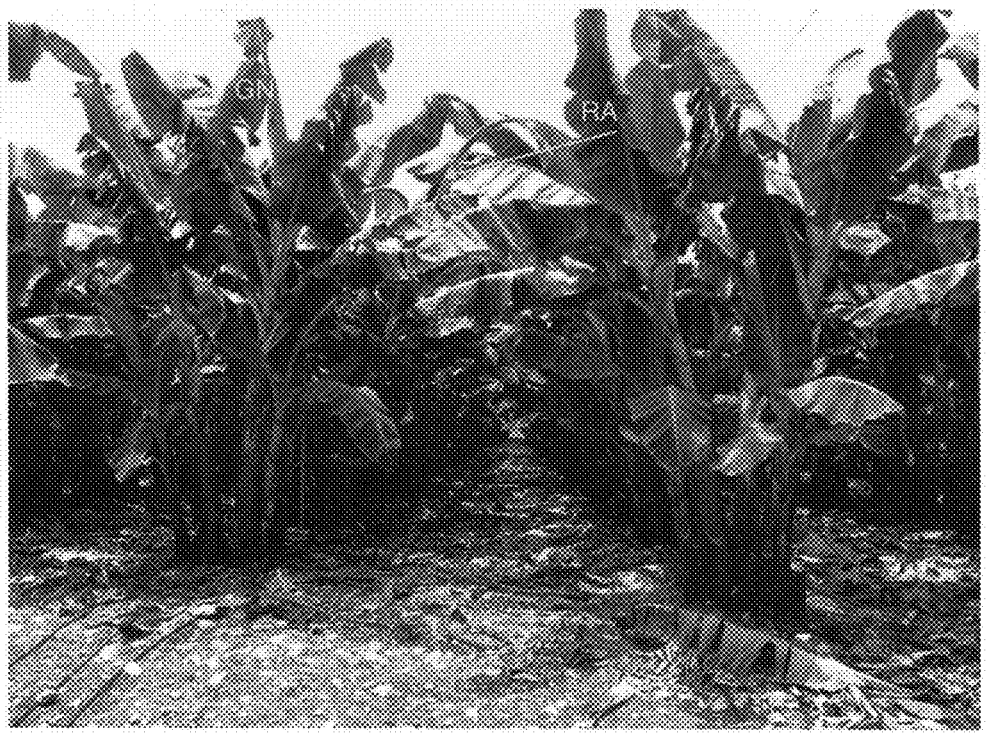
FIG. 4 shows the phenotype of compactly rolled new 'RA' leaves.

FIG. 4: shows the comparison of plant structure of 'GN' and 'RA' grown in the same field side by side approximately 5 months post planting. The plants were produced by tissue culture with the same protocol and transferred to the field approximately 12 weeks after initiation of hardening. The plants of both varieties were planted on the Apr. 15, 2012 and the photo was taken Sep. 15, 2012. Fertigation and other cultural applications were carried out according to commercial banana plantation practices in the Western Galilee (Israel).

Figure 5:
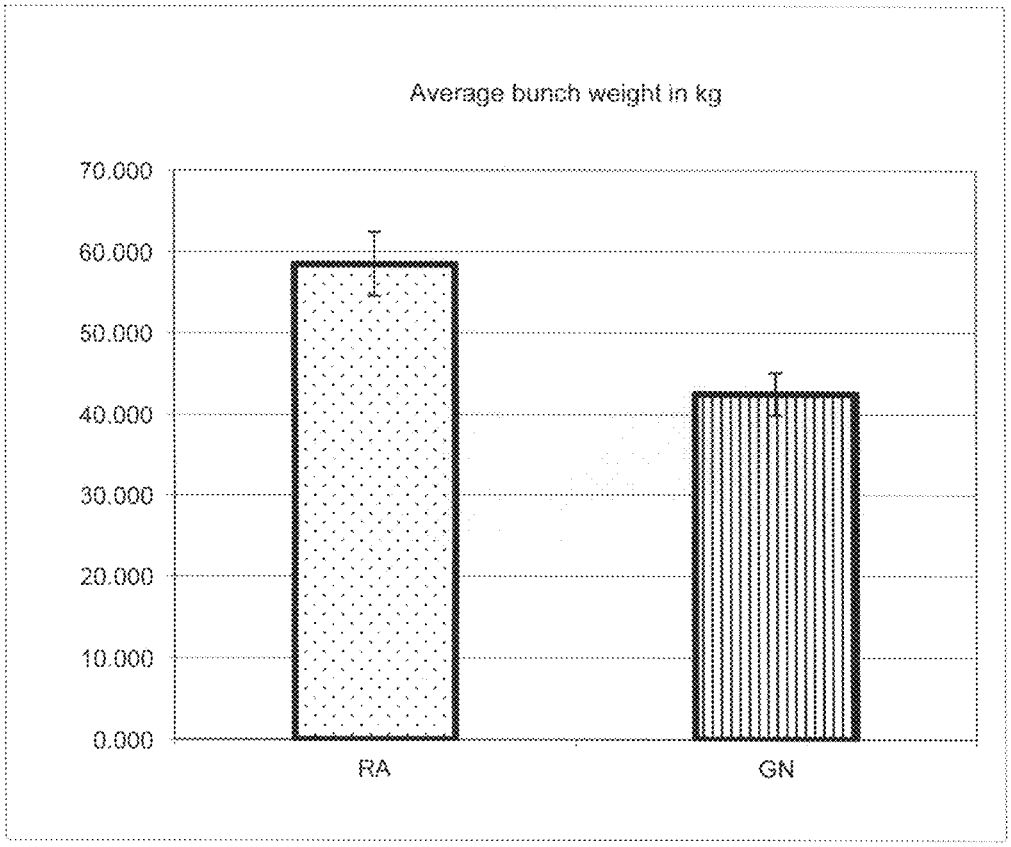
FIG. 5 shows the average bunch weight (kg) of 'RA' and 'GN'.

FIG. 5: shows the average bunch weight (kg) of 'RA' and 'GN' banana (*Musa acuminata* AAA, cv. Cavendish) fruit. The plants described in this patent application were grown under a net in a commercial field in the Western Galilee Israel. Measurements were performed at harvest of the first cycle of production (15 months after planting) in November 2013. Values represent the average bunch weight of the third 4-5 counting from the top (basipatally) from 35 bunches in each of the cultivars 'RA' and 'GN'±standard error. Fertigation and other cultural applications were carried out according to commercial banana plantation practices in the Western Galilee (Israel).

Figure 6:
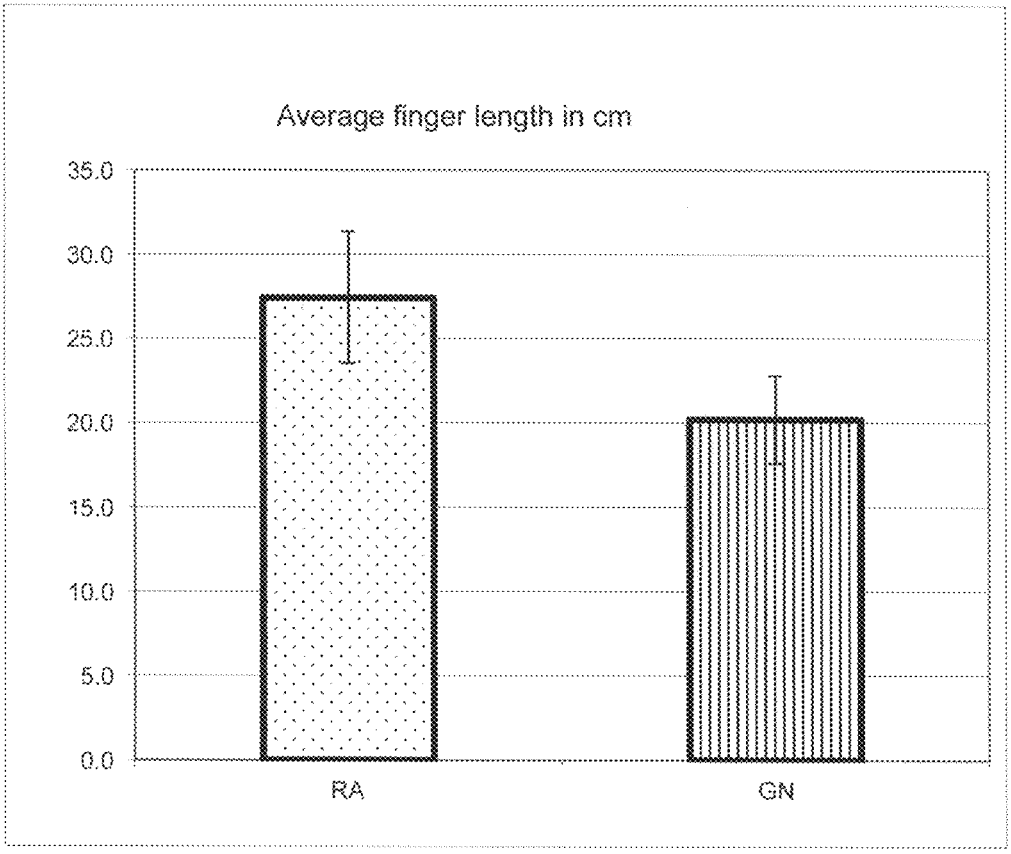
FIG. 6 shows the average finger length (cm) of 'RA' and 'GN' banana fruit.

FIG. 6: shows average finger length (cm) of 'RA' and 'GN' banana fruit. Banana plants (*Musa acuminata* AAA, variety Cavendish) were grown under a net in a commercial field in the Western Galilee Israel. Measurements were performed at harvest of the first cycle of production (15 months after planting) in November 2013. Values represent the average finger length from 35 bunches in each of the selections 'RA' and 'GN'±standard error. Fertigation and other cultural applications were carried out according to commercial banana plantation practices in the Western Galilee (Israel).

It is well known to those of ordinary skill in the art that finger length is a major qualitative factor for the banana export market. In 'RA' both the upper most hand as well as the lower most hand reach premium size of more than 21 cm. The finger length of 'RA' in the middle hand FIG. 6 (hand #5 from the top proximal hand) is approximately 26% higher than 'GN'. In fact, the 'RA' fingers are longer than any other known Cavendish cultivar TABLE 1.

Figure 7:
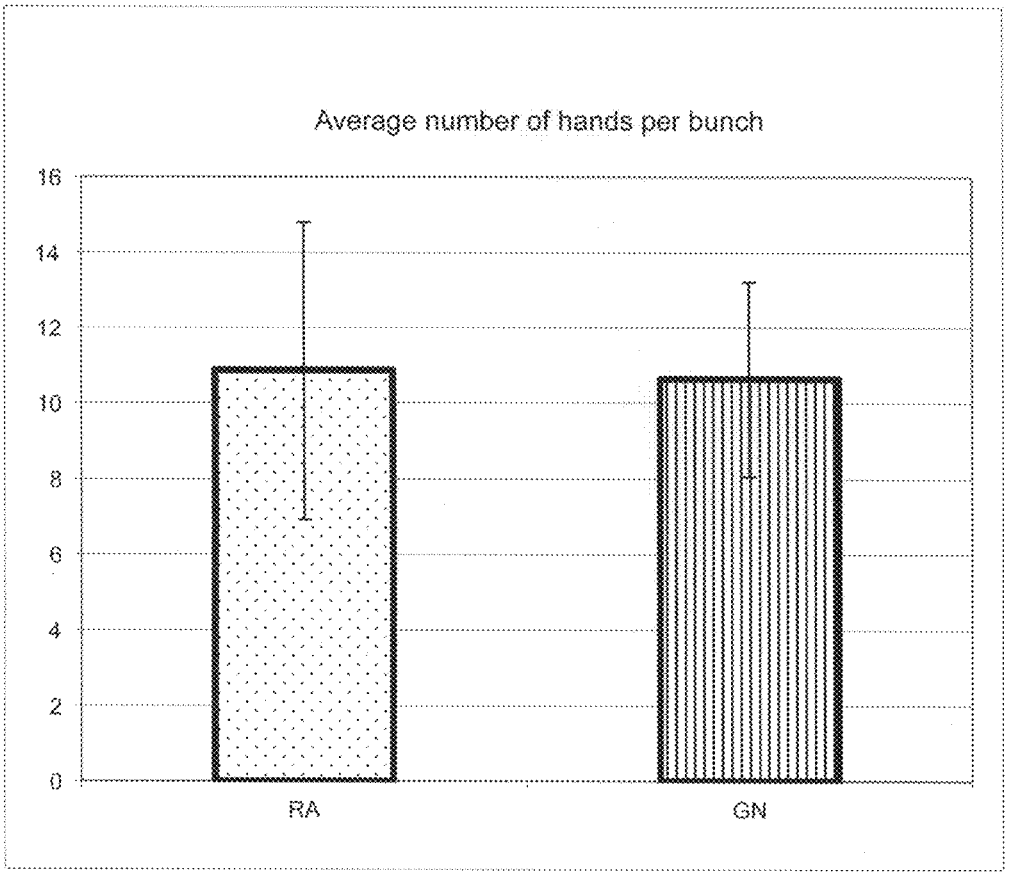
FIG. 7 shows the average number of marketable hands in 'RA' and 'GN' banana bunches.

FIG. 7: shows average number of total hands per bunch in 'RA' and 'GN' banana (*Musa acuminata* AAA, cv. Cavendish) selections. Banana plants were grown under a net in a commercial field in the Western Galilee Israel. Measurements were performed at harvest of the first cycle of production (15 months after planting) in November 2013. Values represent the average number of total hands from 35 plants in each of the selections 'RA' and 'GN'±standard error. Fertigation and other cultural applications were carried out according to commercial banana plantation practices in the Western Galilee (Israel). Although FIG. 7 shows an equal number of hands in 'RA' and 'GN', due to 'RA''s longer fingers, the number of marketable hands in 'RA' is greater than in 'GN' FIG. 12.

Figure 8:
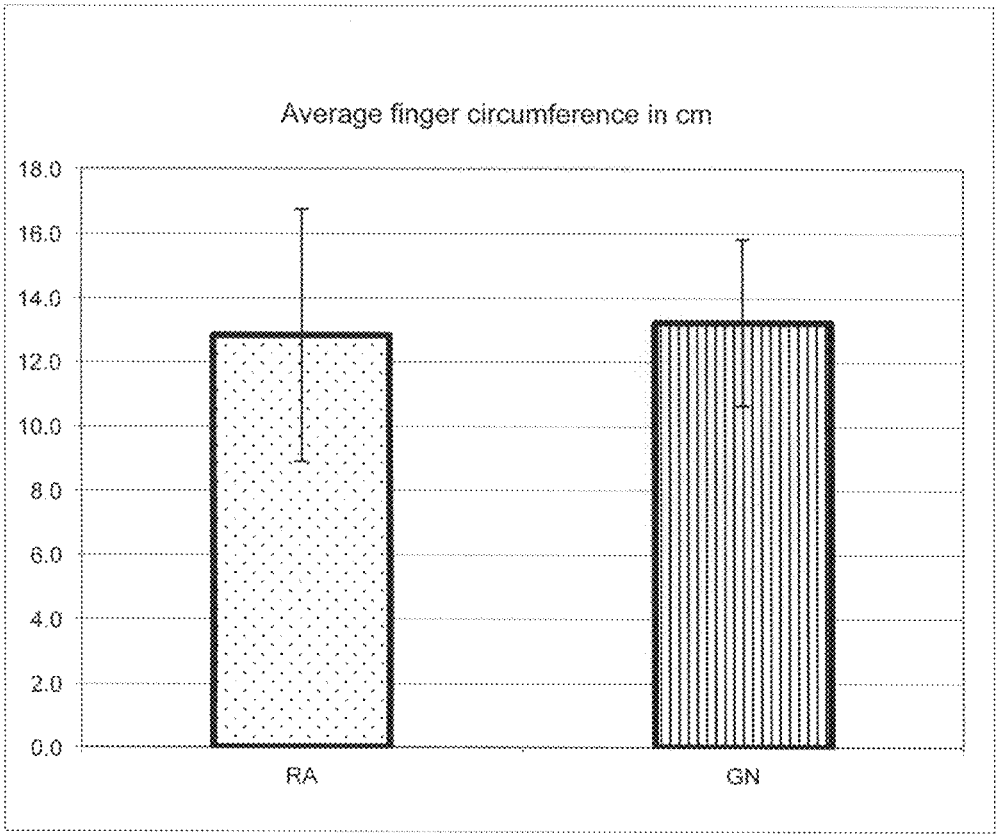
FIG. 8 shows the average finger circumference (cm) of 'RA' and 'GN'.
Figure 10:
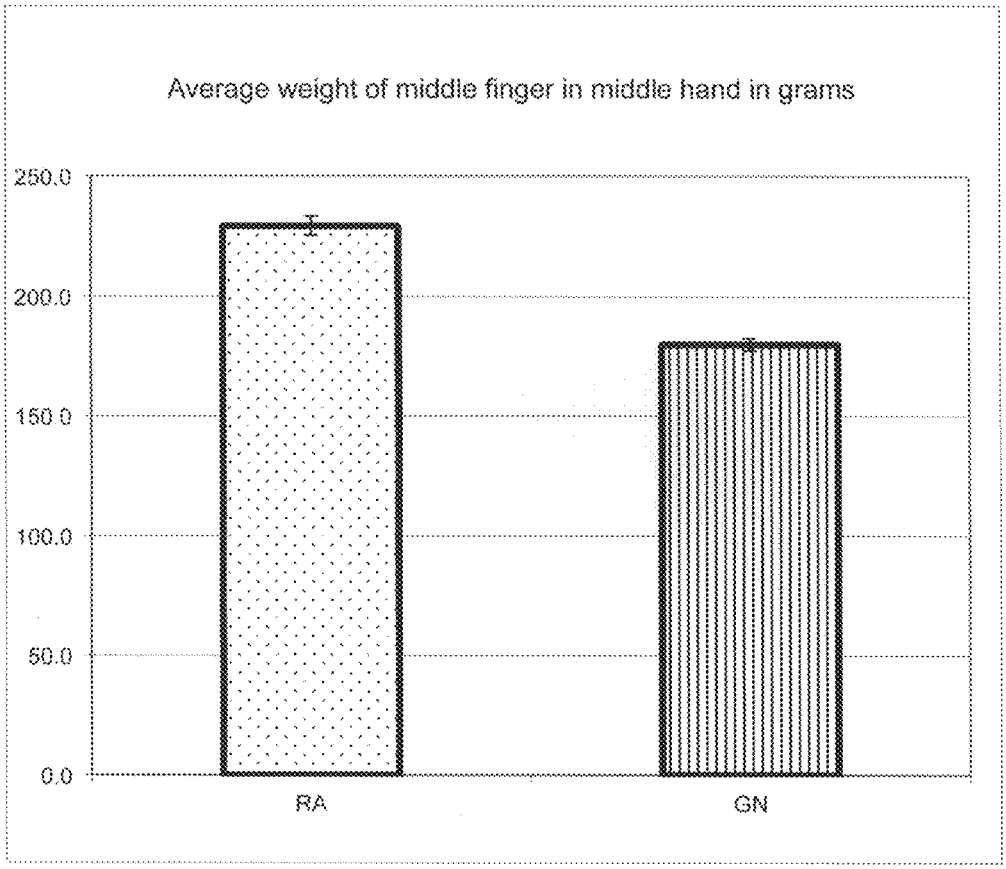
FIG. 10 shows the average finger weight (kg) of the middle finger in the middle hand, of the whorl of fruit facing the internal part of the hand, of 'RA' and 'GN'.

FIG. 8: The average finger circumference (cm) of 'RA' and 'GN' (*Musa acuminata* AAA, variety Cavendish) fruit at time of harvest. The representative finger was selected from middle hand as indicated in FIG. 10. The middle finger in the lower row of fruit was sampled for the measurements. Banana plants were grown under a net in a commercial field in the Western Galilee Israel. Measurements were performed at harvest of the first cycle of production (15 months after planting) in November 2013. Values represent the average finger circumference from 35 plants in each of the selections 'RA' and 'GN'±standard error. Fertigation and other cultural applications were carried out according to commercial banana plantation practices in the Western Galilee (Israel).

Figure 9:
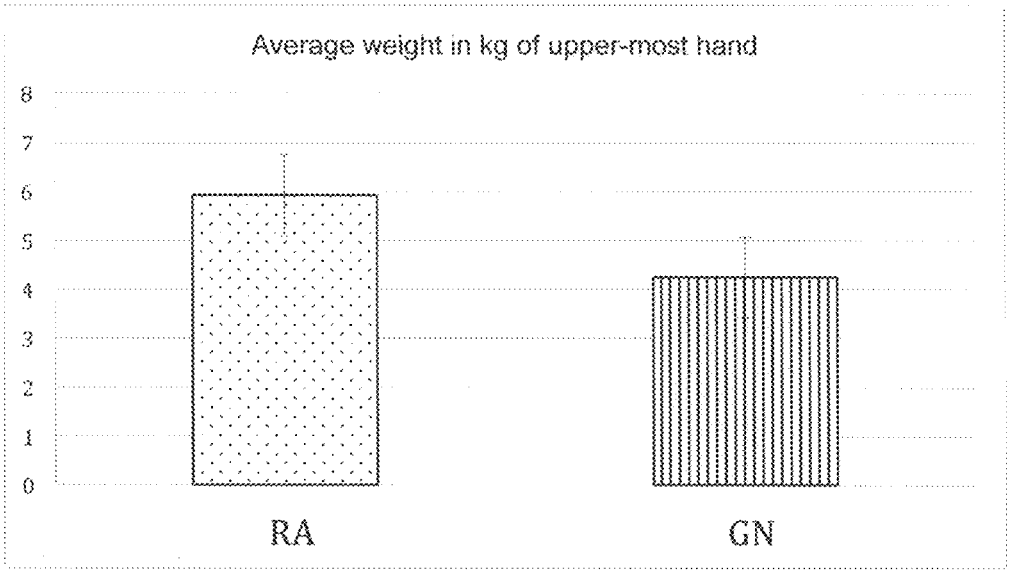
FIG. 9 shows the average weight (kg) of the upper hand of 'RA' and 'GN' banana bunches.

FIG. 9: Average weight (kg) of highest hand on a bunch of banana (*Musa acuminata* AAA, variety Cavendish) cultivars 'RA' and 'GN'. Banana plants were grown under a net in a commercial field in the Western Galilee, Israel. Measurements were performed at harvest of the second cycle of production (15 months after planting) in November 2013. Values represent the average upper most hand weight from 35 plants in each of the selections 'RA' and 'GN'±standard error. Fertigation and other cultural applications were carried out according to commercial banana plantation practices in the Western Galilee, Israel.

FIG. 10: Shows a graph comparing the middle finger of the middle hand between representative middle hands of 'RA' and 'GN'. Each representative hand is the 3rd hand from the inner whorl of the proximal end of the bunch, measured at harvest. Bunches were harvested on Sep. 15, 2013 on a plantation in Western Galilee, Israel. FIG. 10 shows the average weight (g) of the middle finger, the inner whorl of fruit, of the third hand from the top on a bunch of banana (*Musa acuminata* AAA, variety Cavendish) cultivars RA and GN. Banana plants were grown under a net in a commercial field in the Western Galilee, Israel. Measurements were performed at harvest of the second cycle of production (15 months after planting) in November 2013. Values represent the mean hand weight from 35 plants in each of the cultivars RA and GN±standard error. Fertigation and other cultural applications were carried out according to commercial banana plantation practices in the Western Galilee, Israel.

FIG. 11: shows 'RA' grown in the field at a density of 1700 plants per hectare. The plants were produced by tissue culture with the same protocol and transferred to the field approximately 12 weeks after initiation of hardening. The plants of both varieties were planted on the Apr. 15, 2012 and the photo was taken Sep. 15, 2013. Fertigation and other cultural applications were carried out according to commercial banana plantation practices in the Western Galilee (Israel).

Figure 12:
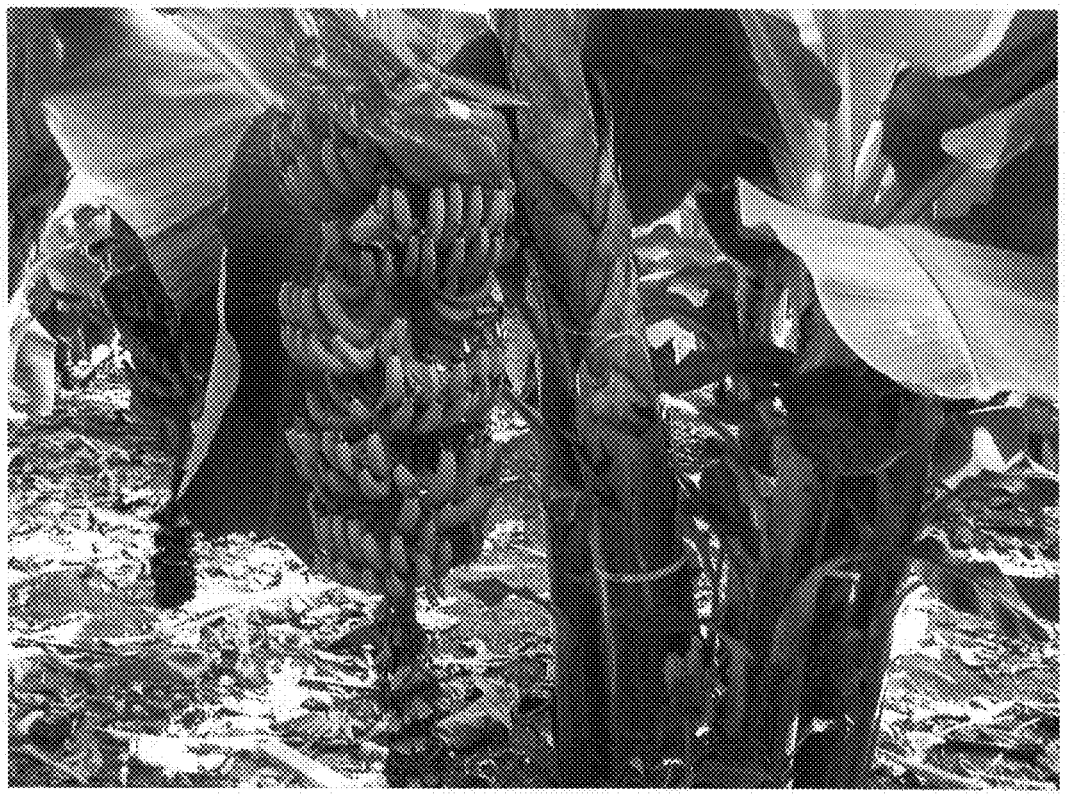
FIG. 12 shows a typical 'GN' banana plant including a fruit bunch approximately one month prior to harvesting.

FIG. 12: shows 'GN' grown in the field at a density of 1700 plants per hectare. The plants were produced by tissue culture with the same protocol and transferred to the field approximately 12 weeks after initiation of hardening. The plants of both cvs. were planted on the Apr. 15, 2012 and the photo was taken Sep. 15, 2013. Fertigation and other cultural applications were carried out according to commercial banana plantation practices in the Western Galilee (Israel).

Figure 13:
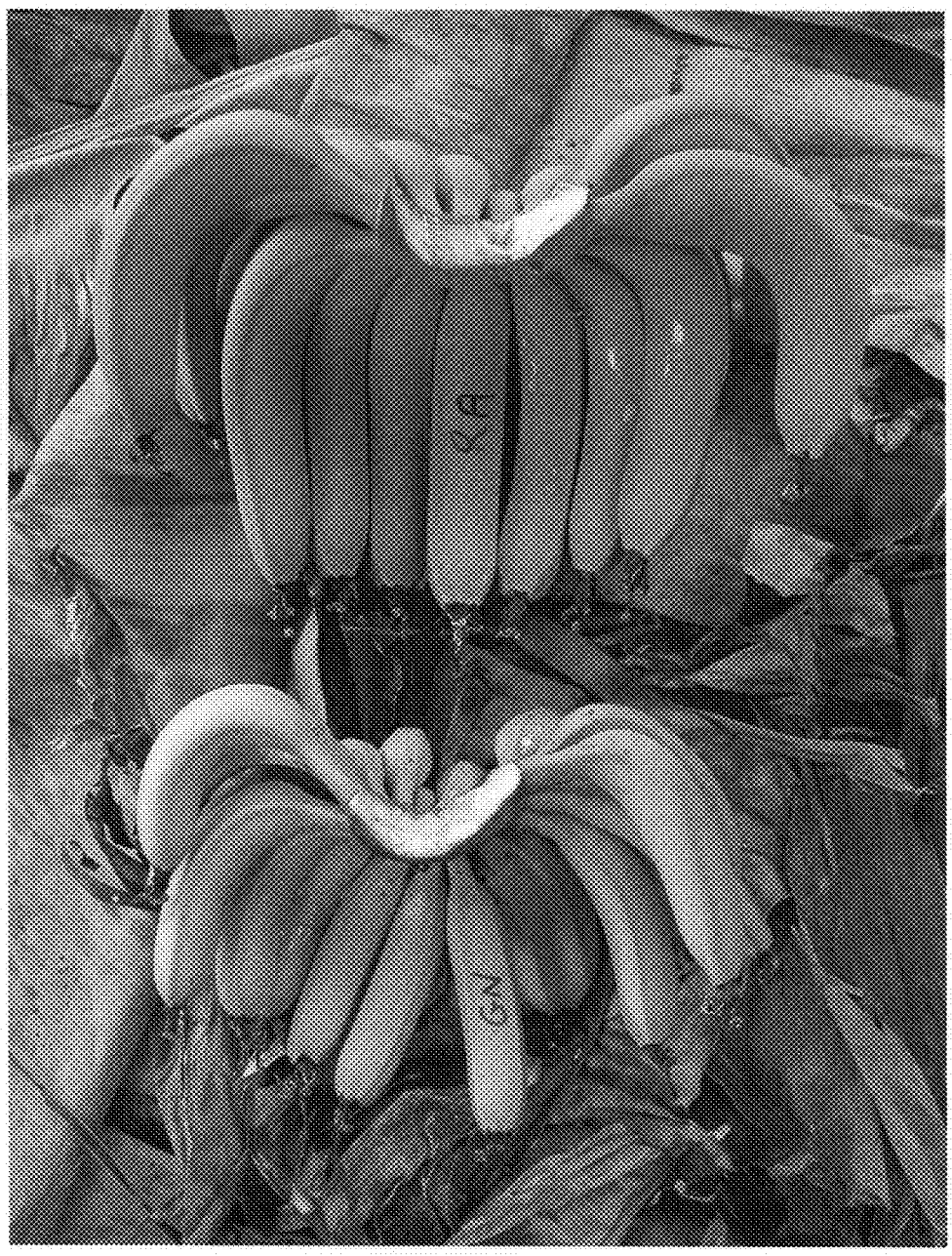
FIG. 13 shows a comparison of hand #12 (counting from the top downwards) in a bunch for both 'Gran Nain' and 'RA'.

FIG. 13, shows a comparison of hand number 12 between 'RA' (top) and 'GN' (bottom). The plants of both cvs. were planted on Apr. 15, 2012, and the photo was taken on Oct. 22, 2013. Fertigation and other cultural applications were carried out according to commercial banana plantation practices in the Western Galilee (Israel).

Figure 14:
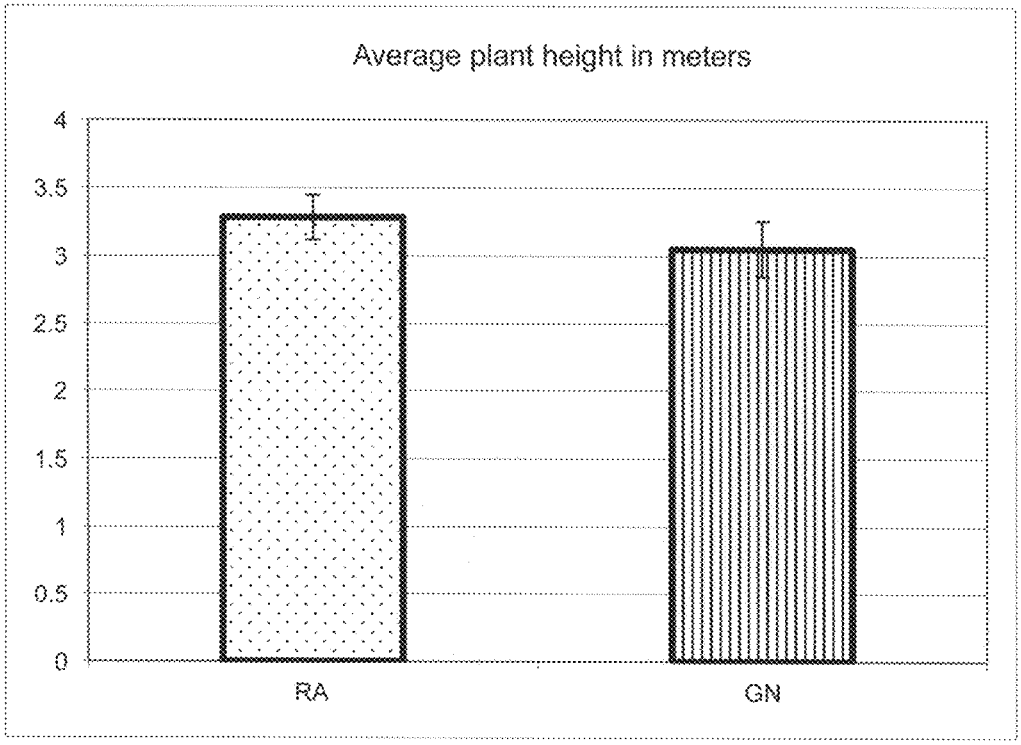
FIG. 14 shows the average height (cm) of 'RA' and 'GN'.

FIG. 14 and Table 1: show average height (cm) of 'RA' and 'GN' banana plants. The average height (cm) of 'RA' and 'GN' banana plants (*Musa acuminata* AAA, cv. Cavendish) measured after completion of flowering, FIG. 14. Banana plants were grown under a net in a commercial field in the Western Galilee Israel. Measurements were performed at harvest of the first cycle of production (15 months after planting) in November 2013. Values represent the average height from soil level to the bent neck of the fruit bunch from 35 plants from each of the cultivars RA and GN±standard error. Fertigation and other cultural applications were carried out according to commercial banana plantation practices in the Western Galilee (Israel). The difference in height, FIG. 14, between 'RA' and 'GN' is approximately 20 cm but is not significant enough to create a problem for the growers.

Figure 15:
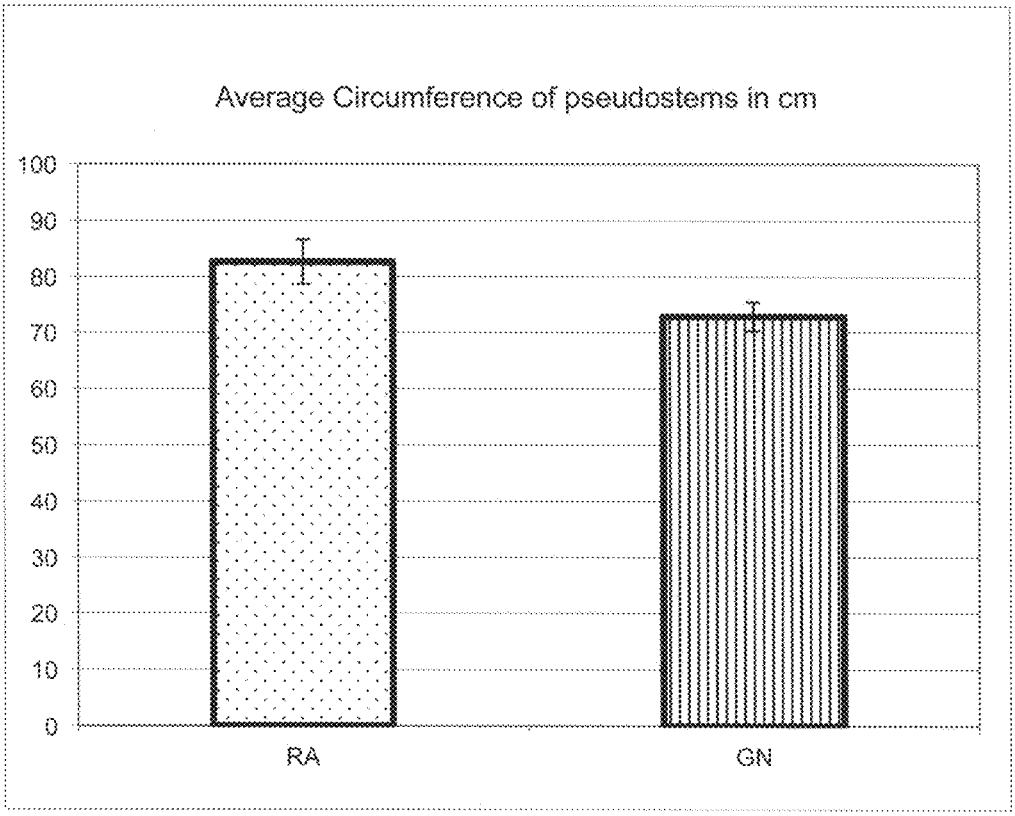
FIG. 15 shows the average circumference of pseudostem (cm) of 'RA' and 'GN' banana plants.

FIG. 15: shows average the circumference of pseudostem (cm) of 'RA' and 'GN' banana plants (*Musa acuminata* AAA, variety Cavendish) measured after completion of flowering. Banana plants were grown under a net in a commercial field in the Western Galilee Israel. Measurements were performed at harvest of the first cycle of production (15 months after planting) in November 2013. Values represent the average circumference at soil level of the pseudostems of 35 plants from each of the selections RA and GN±standard error. Fertigation and other cultural applications were carried out according to commercial banana plantation practices in the Western Galilee (Israel). As shown in FIG. 15, 'RA''s pseudostem circumference is on the average 12% thicker than 'GN' (82 cm v 72 cm respectively).

Figure 16:
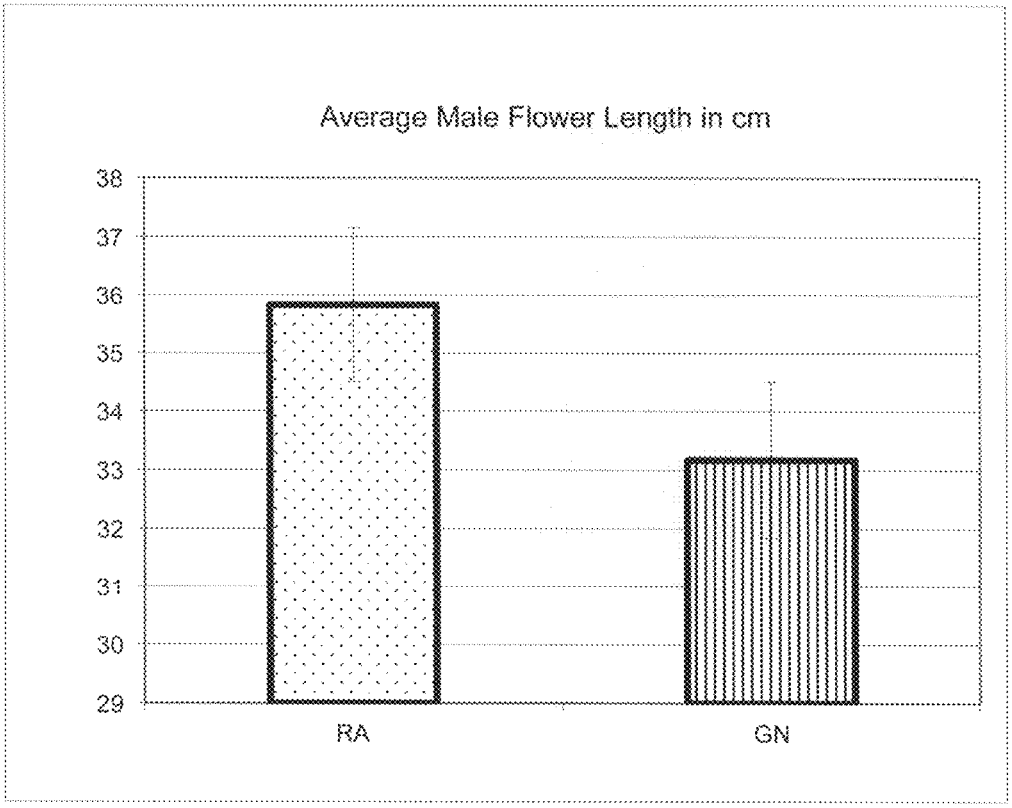
FIG. 16 shows the average length of the male flower (cm) of 'RA' and 'GN'.

FIG. 16: shows the average length of the male flower (cm) of 'RA' and 'GN'. Banana plants were grown under a net in a commercial field in the Western Galilee Israel. Measurements were performed at harvest of the first cycle of production (15 months after planting) in November 2013. Values represent the average finger length from 35 plants in each of the cultivars RA and GN±standard error. Fertigation and other cultural applications were carried out according to commercial banana plantation practices in the Western Galilee (Israel).

Figure 17:
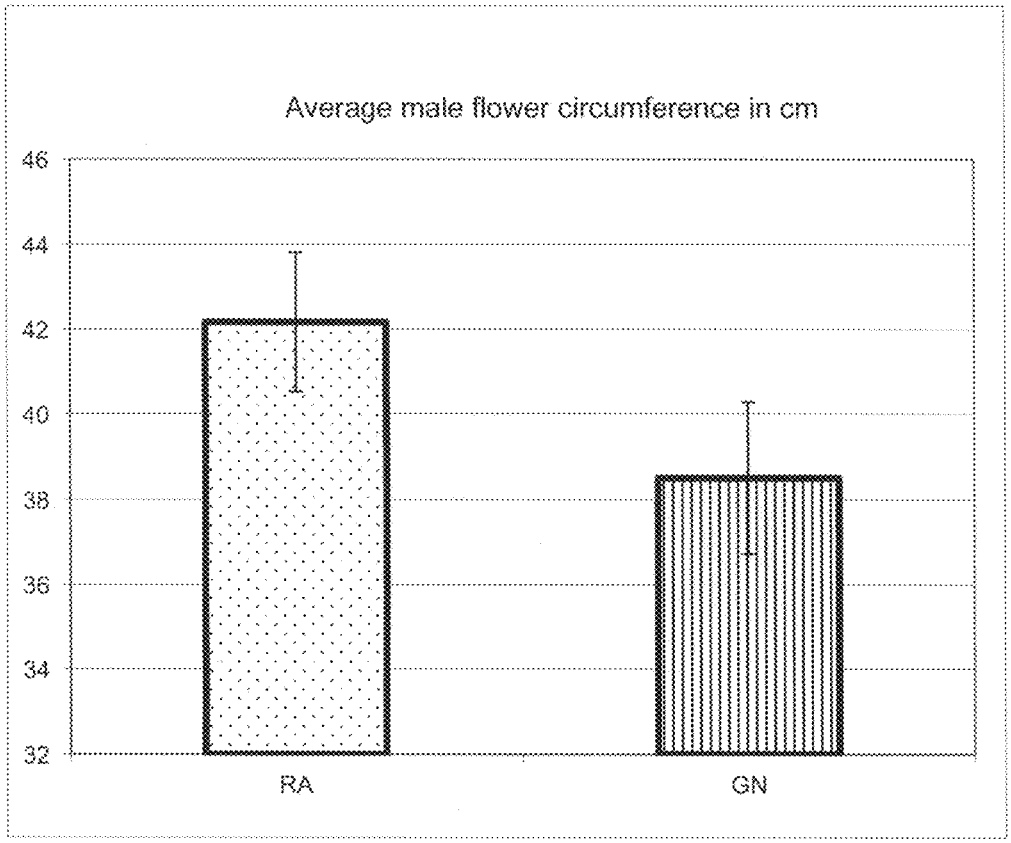
FIG. 17 shows the average circumference (cm) of the male flower of 'RA' and 'GN'.

FIG. 17: shows the average circumference (cm) of the male flower of 'RA' and 'GN'. Banana plants were grown under a net in a commercial field in the Western Galilee Israel. Measurements were performed at harvest of the first cycle of production (15 months after planting) in November 2013. Values represent the average male flower circumference from 35 plants in each of the cultivars RA and GN±standard error. Fertigation and other cultural applications were carried out according to commercial banana plantation practices in the Western Galilee (Israel).

Figure 18:
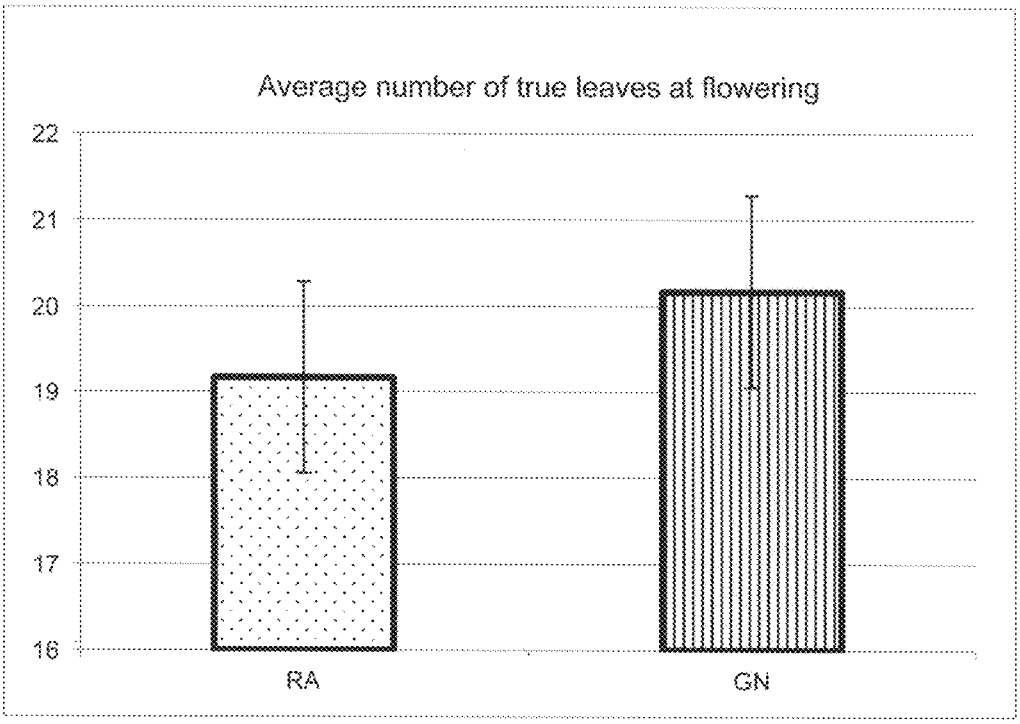
FIG. 18 shows the average number of true leaves of 'RA' and 'GN' at flowering.

FIG. 18: shows the average number of true leaves of 'RA' and 'GN' at flowering. Banana plants were grown under a net in a commercial field in the Western Galilee Israel. Measurements were performed at harvest of the first cycle of production (15 months after planting) in November 2013. Values represent the average number of true leaves from 35 plants in each of the cultivars RA and GN±standard error. Fertigation and other cultural applications were carried out according to commercial banana plantation practices in the Western Galilee (Israel).

Figure 19:
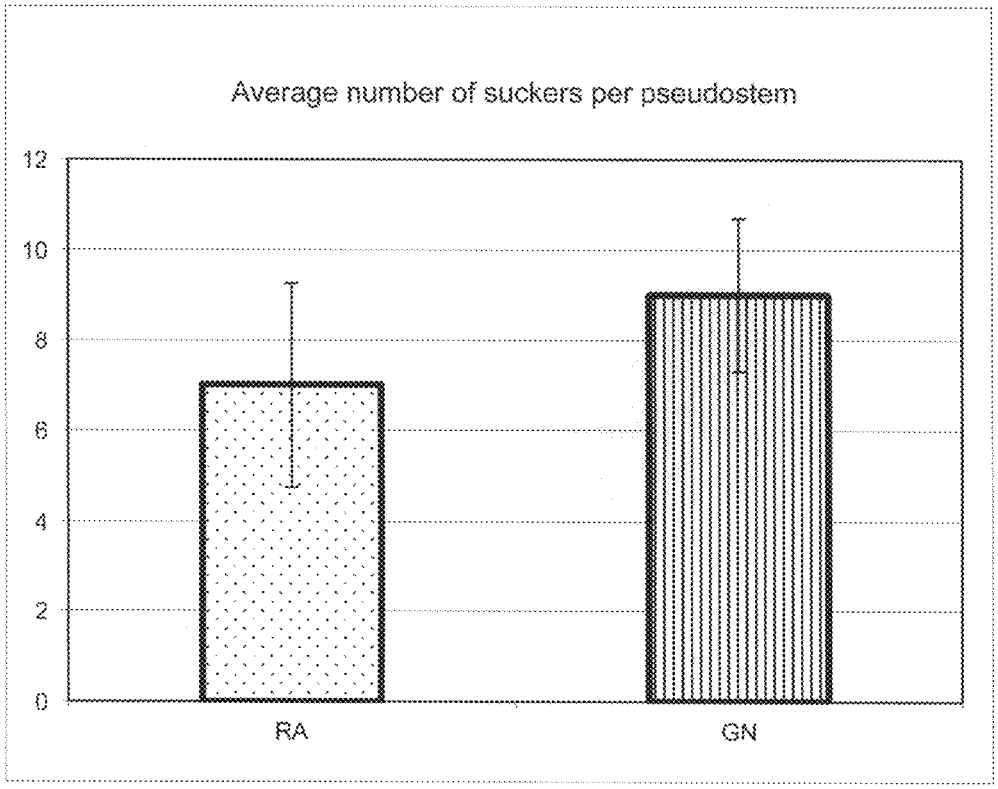
FIG. 19 shows the average number of suckers of 'RA' and 'GN' at the time of the first cycle of the fruit harvest.

FIG. 19: shows the average number of suckers of 'RA' and 'GN' at the time of the first cycle of the fruit harvest. Banana plants were grown under a net in a commercial field in the Western Galilee Israel. Measurements were performed at harvest of the first cycle of production (15 months after planting) in November 2013. Values represent the average number of suckers from 35 plants in each of the cultivars RA and GN±standard error. Fertigation and other cultural applications were carried out according to commercial banana plantation practices in the Western Galilee (Israel).

DETAILED BOTANICAL DESCRIPTION

Detailed botanical description of the new and distinct selection 'RA', which includes its general appearance, pseudostem and suckers, petiole, midrib, leaf, inflorescence and male bud, flower bract, male flower, and fruit. This description is based on observations of specimens grown in the Western Galilee, Israel, 20 months after planting. The plantation is at 18 m above sea level, approximately 800 m east of the Mediterranean Sea, next to the town of Shlomi in the Western Galilee, Israel. The description is based on an observation of approximately 50 plants grown in a commercial plantation. Data was collected between August and September 2012. The descriptors presented herein are in accordance with and include all of the 117 international standards found in "Descriptors for Banana (*Musa* spp.)" elaborated by CIRAD/INIBAP/IPGRI. The color terminology is in accordance with The U.K.'s Royal Horticultural Society's Color Chart, 2001.

Pseudostem:

*Height.*—2 — (2.1 to 2.9 m).

*Ploidy.*—Triploid (AAA).

General appearance:

*Leaf habit.*—2 — Intermediate.

*Aspect.*—67.5 cm (5 plants).

*Pseudostem color.*—Light Green (10 — 164C).

*Appearance.*—2 — Shiny (not waxy).

*Pigmentation of the underlying pseudostem.*—1 — Pink-Purple (60A).

*Sap color.*—1 Green (144C).

*Wax on leaf sheaths.*—1 — No visible signs of wax.
*Number of suckers.*—7.
*Position of suckers.*—2 — Close to parent (vertical growth).

Petiole:
*Blotches at petiole base.*—4 — Extensive pigmentation.
*Blotches color.*—2 — Dark Brown (200B).
*Petiole canal leaf III.*—2 — Wide with erect margins.
*Petiole margins.*—2 — Winged and not clasping the pseudostem.
*Wing type.*—2 — Not dry.
*Petiole wing color.*—1 — Green (144C).
*Petiole margin color.*—1 — Green (144C).
*Edge of petiole margin.*—2 — With a color line along Pink-purple (60A).
*Entire petiole color.*—Green (144C).
*Petiole margin width.*—2 — >1 cm. Typical observed width=1.4 cm.
*Petiole length.*—1 — <50 cm. Typical observed length=40 cm.

Leaf blade:
*Length.*—2 — 171 to 220 cm.
*Leaf blade width.*—3 — 81 to 90 cm.
*Leaf ratio.*—5 — 2.4 to 2.6.
*Petiole length.*—1 — <50 cm.
*Color of leaf upper surface.*—3 — Green (137B).
*Appearance of leaf upper surface.*—1 — Dull (137C).
*Leaf apex shape.*—Retuse.
*Color of leaf lower surface.*—3 — Green.
*Appearance of leaf lower surface.*—1 — Dull.
*Wax on leaves.*—1 — No visible sign of wax.
*Insertion point of leaf blades on petiole.*—2 — Asymmetric.
*Shape of leaf blade base.*—3 — Both sides pointed.
*Leaf corrugation.*—1 — Even, smooth.
*Color of midrib ventral surface.*—Green (146C).
*Color of midrib dorsal surface.*—Green (137C).
*Color of cigar leaf dorsal surface.*—2 — Light green (145C).
*Ventral venation colour.*—Green (146C).
*Dorsal venation colour.*—Green (137C).
*Blotches on leaves of water suckers.*—1 — Without blotches.

Inflorescence/male bud:
*Peduncle length.*—2 — 31-60 cm.
*Empty nodes on peduncle.*—0.
*Peduncle width.*—3 — >13 cm (average=22 cm).
*Peduncle color.*—3 — Dark green (137C).
*Peduncle hairiness.*—3 — Very hairy, short hairs.
*Bunch position.*—2 — Slightly angled.
*Bunch shape.*—1 — Cylindrical.
*Bunch appearance.*—2 — Compact.

Rachis:
*Type.*—2 — Present.
*Position.*—1 — Falling vertically.
*Male bud type.*—1 — Normal (present).
*Male bud shape.*—4 — Ovoid.
*Male bud length.*—2 — 21-30 cm.
*Diameter of male bud.*—>31 cm (mean value=42 cm. for 6 plants).
*Male bud color.*—Brown-Rusty Brown (166A).

Bract:
*Base shape.*—2 — Medium. (As per Descriptor No. 6.5.1).
*Base descriptor.*—Lifting 2 or more at a time.
*Bract apex shape.*—2 — Slightly pointed.
*Color of the bract external face.*—5 — Purple-brown (166A).
*Color of the bract internal face.*—3 — Orange-Red (169A).
*Color stripes on bract.*—2 — With discolored lines on the external face.
*Bract scars on rachis.*—1 — Very prominent.
*Fading of color on bract base.*—1 — Color discoloring towards the base.
*Male bract shape.*—3 — Ovate.
*Typical width of bract.*—12 cm.
*Typical length of bract.*—20 cm.
*Male bract lifting.*—3 — Lifting two or more at a time.
*Bract behavior before falling.*—1 — Revolute.
*Wax on the bract.*—1 — No visible sign of wax.
*Presence of grooves on the bract.*—2 — Moderate grooving.
*Number of bracts.*—12-15.

Male flower: Data taken at completion of flower emergence.
*Male flower behavior.*—3 — Falling after the bract.
*Compound tepal basic color.*—3 — Yellow (7A).
*Typical tepal number.*—15.
*Margin.*—3 — Yellow (7A).
*Compound tepal pigmentation.*—2 — Rust-colored spots (172A).
*Lobe color of compound tepal.*—2 — Yellow (7A).
*Free tepal appearance.*—3 — 15 folding under apex (corrugated).
*Length typical tepal length.*—5.5 cm.
*Width typical tepal width.*—6 mm.
*Style shape.*—1 — Straight.
*Stigma color.*—1 — Cream (158D).
*Ovary basic color.*—2 — Cream (158C).
*Ovary pigmentation.*—1— No visible sign of pigmentation.

Fruit:
*Position.*—3 — Curved upwards (obliquely, at a 45° angle upward).
*Number of fruit per hand.*—2 — 13-16.
*Fruit length.*—4 — 26-30 cm.
*Fruit shape longitudinal curvature.*—3 — Sharp curve.
*Fruit circumference.*—12.5 cm.
*Fruit pedicel length.*—3 — 24 mm.
*Pedicel diameter.*—14 mm.
*Pedicel color.*—Green (144A).
*Pedicel surface.*—2 — Hairy.
*Immature fruit peel color.*—6 — Dark green (144A).
*Mature fruit peel color.*—2 — Bright yellow (14C).
*Fruit peel thickness.*—2 — 3 mm or more.
*Adherence of the fruit peel.*—1 — Fruit peels easily.
*Cracks in fruit peel.*—1 — Without cracks.
*Pulp in fruit.*—2 — With pulp.
*Pulp color before maturity.*—1 — White (158D).
*Pulp color at maturity.*—2 — Cream (156B).
*Typical fruit weight.*—229 g.
*Fruit is eaten.*—Ripe.
*Flesh texture.*—1 — Firm.
*Predominant taste.*—3 — Sweet.
*Main use.*—Dessert banana.
*Presence of seed.*—No seeds.

Agronomic characteristics: Averages taken during 2012 for second crop in a plot of 1800 plants per hectare.
*Number of leaves at flowering.*—19.

*Average bunch weight.*—35.6 kg.

*Number of hands.*—14, of which 9 are commercial grade.

*Finger length.*—Average 26.6 cm.

*Average number of fingers per hand.*—16.

It is claimed:

1. 'RA', a new and distinct cultivated variety of banana plant, substantially as illustrated and described, that forms a super heavy bunch, especially long, and heavy fingers, with more fingers per hand, wavy leaf lamina, with the youngest leaves tightly rolled, thicker pseudostem circumference, a higher fruit yield per bunch, and a more cylindrical bunch shape than 'Gran Nain'.

* * * * *